US008790660B2

(12) United States Patent
O'Connell et al.

(10) Patent No.: US 8,790,660 B2
(45) Date of Patent: Jul. 29, 2014

(54) **VACCINE AGAINST *EHRLICHIA CANIS***

(75) Inventors: Kevin A. O'Connell, Omaha, NE (US);
Rangappa Narayana Ramachandra, Sinking Spring, PA (US); Stephen David Gaunt, Baton Rounge, LA (US);
Richard E. Corstvet, Gonzales, LA (US); Terri L. Wasmoen, Omaha, NE (US)

(73) Assignees: Intervet Inc., Summit, NJ (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/805,490

(22) PCT Filed: Jun. 29, 2011

(86) PCT No.: PCT/US2011/042323
§ 371 (c)(1),
(2), (4) Date: May 8, 2013

(87) PCT Pub. No.: WO2012/003205
PCT Pub. Date: Jan. 5, 2012

(65) Prior Publication Data
US 2013/0224247 A1    Aug. 29, 2013

Related U.S. Application Data

(60) Provisional application No. 61/360,969, filed on Jul. 2, 2010.

(51) Int. Cl.
*A61K 39/02* (2006.01)
*A61K 49/00* (2006.01)
*A61K 39/00* (2006.01)

(52) U.S. Cl.
USPC ........ 424/234.1; 424/9.1; 424/9.2; 424/184.1

(58) Field of Classification Search
USPC .............................. 424/9.1, 9.2, 184.1, 234.1
See application file for complete search history.

(56) References Cited

U.S. PATENT DOCUMENTS

| 4,579,945 | A | * | 4/1986 | Schwartzman et al. | ...... 536/127 |
| 5,869,335 | A | | 2/1999 | Munderloh et al. | |
| 2005/0202046 | A1 | * | 9/2005 | Hu et al. | ................... 424/234.1 |
| 2006/0188524 | A1 | | 8/2006 | Hu et al. | |

FOREIGN PATENT DOCUMENTS

| WO | 2005/087803 A1 | 9/2005 |
| WO | 2009/036177 A1 | 3/2009 |

OTHER PUBLICATIONS

Mahan, S. et al. Onderstepoort Journal of Veterinary Research, vol. 72, pp. 119-128, 2005.*
McBride, J.W., et al. Expert Reviews in Vaccines vol. 9, No. 9, pp. 1071-1082, 2010.*
Breitschwerdt et al., "Doxycycline Hyclate Treatment of Experimental Canine Ehrlichiosis Followed by Challenge Inoculation with Two *Ehrlichia canis* Strains", Antimicrobial and Chemotherapy, 1998, pp. 362-368, vol. 42(2).
Dawson et al., "Serologic Diagnosis of Human Ehrlichiosis Using Two *Ehrlichia cals* Isolates", The Journal of Infectious Diseases, 1991, pp. 564-567, vol. 163.
Gaunt et al., "Isolation of *Ehrlichia canis* from Dogs following Subcutaneous Inoculation", Journal of Clinical Microbiiology, 1996, pp. 1429-1432, vol. 34(8).
Harrus et al., "Down-regulation of MHC class II receptors of DH82 cells, following infection with *Ehrlichia canis*", Veterinary Immunology and Immunopathology, 2003, p. 239-243, vol. 96.
Keysary et al., "Cultivation of *Ehrlichia canis* in a continuous BALB/C mouse macrophase cell culture line", Journal of Veterinary Diagnostic, 2001, pp. 521-523, vol. 13.
Mahan et al., "A preliminary study to evaluate the immune responses induced by immunization of dogs with inactivated *Ehrlichia canis* organisms", Onderstepoort Journal of Veterinary Research, 2005, pp. 119-128, vol. 72.
Nyindo et al., "Tropical Canine Pancytopenia: in Vitor Cultivation of the Causative Agent—*Ehrlichia canis*", American Journal of Veterinary Research, 1971, pp. 1651-1658, vol. 32.
Rhim, Johng S., "Development of Human Cell Lines from Multiple Organs", Annals of the New York Academy of Sciences, 2000, pp. 16-25, vol. 919.
Singu et al., "Unique macrophage and tick cell-specific protein expression from the p28/p30-outer membrane protein multigene locus in *Ehrlichia chaffeensis* and *Ehrlichia canis*", Cellular Microbiology, 2006, pp. 1475-1487, vol. 8(9).
Stephenson et al., "Canine Peritoneal Macrophages: Cultivation and Infections with *Ehrlichia canis*", American Journal of Veterinary Research, 1977, pp. 1815-1819, vol. 38.
Stephenson et al., "Somatic Cell Hybrids of Canine Peritoneal Macrophages and SV40-Transformed Human Cells: Derivation, Characterization, and Infections with *Ehrlichia canis*", American Journal of Veterinary Research, 1980, pp. 234-240, vol. 41.
Wellman et al., "A Maorophage-Monocyte Cell Line From a Dog With Malignant Histiocytosis", In Vitro Cellular & Develomental Biology, 1986, pp. 223-228, vol. 24.
International Search Report for corresponding PCT/US2011/042323, mailed on Jan. 12, 2012.

* cited by examiner

*Primary Examiner* — Rodney P Swartz

(57) ABSTRACT

Vaccine and/or immunogenic compositions that comprise an effective immunizing amount of an antigen from *E. canis* are described. In addition, methods of immunizing a subject against *E. canis* by providing the vaccine and/or immunogenic compositions are also disclosed.

18 Claims, 5 Drawing Sheets

VACCINE AGAINST *EHRLICHIA CANIS*

CROSS-REFERENCE TO RELATED APPLICATIONS

This application is a national stage entry under 35 U.S.C. §371 of PCT/US2011/0423, filed on Jun. 29, 2011, which claims priority under 35 U.S.C. §119(e) of provisional application U.S. Ser. No. 61/360,969 filed Jul. 2, 2010, the contents of which are hereby incorporated by reference in their entirety.

FIELD OF THE INVENTION

The present invention relates to immunogenic compositions and to vaccines against Canine Monocytic Ehrlichiosis (CME) caused by the bacterium *Ehrlichia canis* and associated methods.

BACKGROUND

Canine monocytic ehrlichiosis (CME) is a severe rickettsial disease in dogs caused by the bacteria *Ehrlichia canis* (*E. canis*). *E. canis* is spread from dog to dog via the Brown Dog Tick (*Rhipicephalus sanguineus*). Following an incubation period of 2 to 3 weeks post-infection, dogs may progress through acute, subclinical, and chronic phases of the disease. In the acute phase, clinical signs range from mild to severe thrombocytopenia, leukopenia, anemia, lethargy, and weight loss. After two months, most dogs will enter a subclinical phase lasting months or years, during which low blood values may persist, but clinical signs are minimal. A small percentage of infected dogs may develop a severe form of the disease known as Tropical Canine Pancytopenia (TCP). Persistent bone marrow depression, hemorrhages, neurological disturbances, peripheral edema, and severe weight loss are characteristic of TCP. Hypotensive shock may develop, leading to death. Despite reports of immunogenic compositions against *E. canis* [see, e.g., Mahan et al., *Onderstepoort J. Vet. Res.* 72(2): 119-128 (2005); US 2006/0188524A1] heretofore, there has been no demonstration of an effective vaccine against *E. canis*. Therefore, there is a need for vaccines that protect against CME and/or TCP.

The citation of any reference herein should not be construed as an admission that such reference is available as "Prior Art" to the instant application.

BRIEF SUMMARY OF THE INVENTION

The present invention provides vaccines and/or immunogenic compositions to promote a protective immune response against a cause of ehrlichiosis. In certain embodiments, a vaccine composition and/or an immunogenic composition comprises an agent that when administered as a primary vaccine to a subject elicits minimal, if any, humoral immune response in the subject. In particular embodiments, the immunogenic composition comprises an agent that when administered as a primary vaccine elicits minimal, if any, humoral immune response in the subject, but still elicits a protective immune response. One such embodiment is a vaccine that comprises an inactivated *E. canis* grown on a dog bone marrow cell line. In particular embodiments of this type, the vaccine can further comprise an adjuvant. In certain embodiments of this type, the adjuvant is Cord Factor. In more particular embodiments, a Cord Factor adjuvant is dissolved in a chloroform solvent system.

In one aspect, the present invention provides a vaccine composition and/or an immunogenic composition that comprises an antigen from *E. canis* that upon an initial administration to a subject (e.g., as a primary vaccine) does not elicit the production of significant antibody against the antigen. Accordingly, certain embodiments of the present invention include immunogenic compositions and/or vaccine compositions that comprise an effective immunizing amount of antigen from *E. canis* in which an initial administration/primary vaccine of the composition to a subject elicits a minimal humoral response. In particular embodiments the present invention provides an immunogenic composition and/or vaccine that after initial administration/primary vaccination does not elicit a measurable humoral response, while eliciting a protective immune response in a subject. In certain embodiments a vaccine and/or immunogenic composition of the present invention in a primary vaccination/initial administration elicits a cellular immune response, while eliciting a minimal and/or unmeasureable (e.g., undetectable) humoral response.

Therefore in a related aspect, the present invention provides a vaccine composition that comprises an effective immunizing amount of an antigen from *E. canis*. In certain embodiments of this type, the antigen elicits a protective immune response, but elicits a minimal humoral response in a subject when the vaccine is administered as a primary vaccine. Vaccines and/or an immunogenic compositions of the present invention can comprise an antigen that is generated from *E. canis* grown and/or passaged on a cell as disclosed herein. In certain embodiments, the *E. canis* is grown and/or passaged on a canine cell line. In more particular embodiments the cell line can be a dog bone marrow cell line. In more particular embodiments the cell has the ATCC accession No. PTA-10545, and/or one having one or more, and/or all of the identifying characteristics of the cell that has ATCC accession No. PTA-10545. In a particular embodiment, the *E. canis* antigen is a cell-associated *E. canis* that has the ATCC accession No. PTA-10546, and/or one having one or more, and/or all of the identifying characteristics of the cell-associated *E. canis* that has the ATCC accession No. PTA-10546.

The present invention further provides a cell-associated *E. canis* that has the ATCC accession No. PTA-10546. The present invention also provides a cell-associated *E. canis* that has one or more, and/or all of the identifying characteristics of the cell-associated *E. canis* that has the ATCC accession No. PTA-10546. In addition, the present invention provides a cell that has the ATCC accession No. PTA-10545. The present invention further provides a cell that has one or more, and/or all of the identifying characteristics of the cell that has the ATCC accession No. PTA-10545.

In addition, the *E. canis* antigens of the vaccines and/or immunogenic compositions of the present invention can be inactivated. In certain embodiments the inactivated *E. canis* antigen is inactivated with formal in.

In another aspect, the present invention provides vaccines and/or an immunogenic compositions that comprise an adjuvant. In certain embodiments of this type, the adjuvant is a lipophilic adjuvant. In certain embodiments, the lipophilic adjuvant is within a non-polar solvent. In particular embodiments an immunogenic composition and/or vaccine of the present invention comprises an antigen that can be combined with a hydrophobic adjuvant and is made miscible with a polar solvent system comprised by the vaccine and/or an immunogenic composition. In more particular embodiments the adjuvant comprises a Chord factor such as a trehalose 6,6'-dimycolate. In particular embodiments, trehalose 6,6'-dimycolate is within a non-polar solvent. In more particular embodiments the adjuvant comprises trehalose 6,6'-dimycolate dissolved in a chloroform solvent system. In particular embodiments the chloroform solvent system comprises about 65-95% chloroform volume/volume. In more particular embodiments the chloroform solvent system comprises about 80-95% chloroform volume/volume. In particular embodiments the chloroform solvent system comprises about 5.0-30% methanol volume/volume. In more particular embodiments the chloroform solvent system comprises about 7.5-15% methanol volume/volume. In particular embodiments the chloroform solvent system comprises about 0.5-5.0% water volume/volume. In more particular embodiments the chloroform solvent system comprises about 0.75-2.5% water volume/volume. In certain embodiments, the chloroform solvent system comprises about 90% chloroform:10% methanol:1.0% water volume to volume, respectively. In particular embodiments the vaccine and/or immunogenic composition comprises a formalin-inactivated cell-associated *E. canis* grown in the deposited cells having the ATCC accession No. PTA-10545 and an adjuvant comprising trehalose 6,6'-dimycolate dissolved in 90:10:1 chloroform:methanol:water. A composition comprising a Chord factor, such as trehalose 6,6'-dimycolate, dissolved in a chloroform solvent system is also part of the present invention, as is its use as an adjuvant.

In addition, the present invention provides *E. canis* bacteria grown on cells and/or cell lines that are particularly suitable for its growth. The present invention further provides processes for producing an antigen for a vaccine and/or immunogenic composition of the present invention. Thus, the present invention provides processes for producing *E. canis* antigens. In particular embodiments the *E. canis* is grown on a macrophage. In certain embodiments the *E. canis* bacteria are grown on a macrophage-like cell line. In certain embodiments *E. canis* is grown on a Dog Bone Marrow (DBM) cells to produce a cell-associated *E. canis* antigen. In particular embodiments the *E. canis* bacteria are grown on a DBM cell line. In particular embodiments that DBM cell line is DBM (WCS) MCS+12, ATCC accession No. PTA-10545. In particular embodiments the *E. canis* is cell-associated, WS MS+3, 19517-001ATCC accession No. PTA 10546. In alternative embodiments, *E. canis* is grown on a DH-82 cell line.

An *E. canis* antigen of the present invention can be an inactivated *E. canis*. In particular embodiments the *E. canis* antigen is a bacterin. In certain embodiments, the inactivated *E. canis* antigen is cell-associated.

The present invention also provides methods of immunizing a subject against *E. canis*. Such methods can include administering to a subject a vaccine composition and/or an immunogenic composition of the present invention. Certain embodiments comprise administering a vaccine and/or immunogenic composition according to the invention to the subject intradermally. Another such method comprises administering a vaccine and/or immunogenic composition according to the invention to the subject subcutaneously. Still another such method comprises administering a vaccine and/or or immunogenic composition according to the invention to the subject orally. In particular embodiments of this type, the animal subject is a canine. In another embodiment, the animal subject is a feline (e.g., a housecat). In particular embodiments a second dose of the vaccine composition and/or immunogenic composition is provided as a booster. In certain embodiments the booster is administered about 21 days after the initial dose of the vaccine composition.

The present invention further provides a method of making the vaccine compositions and/or immunogenic compositions of the present invention. In certain embodiments the present invention provides a process for producing an *E. canis* antigen as described herein. The vaccine compositions and/or immunogenic compositions are prepared by admixing an antigen of the present invention with a veterinarily suitable excipient. In certain embodiments of this type the antigen is a cell-associated *E. canis* bacterin. In particular embodiments, the veterinarily suitable excipient is a Cord Factor adjuvant dissolved in a chloroform solvent system.

These and other aspects of the present invention will be better appreciated by reference to the Drawings, Detailed Description and Examples.

DETAILED DESCRIPTION OF THE INVENTION

Figure 1:
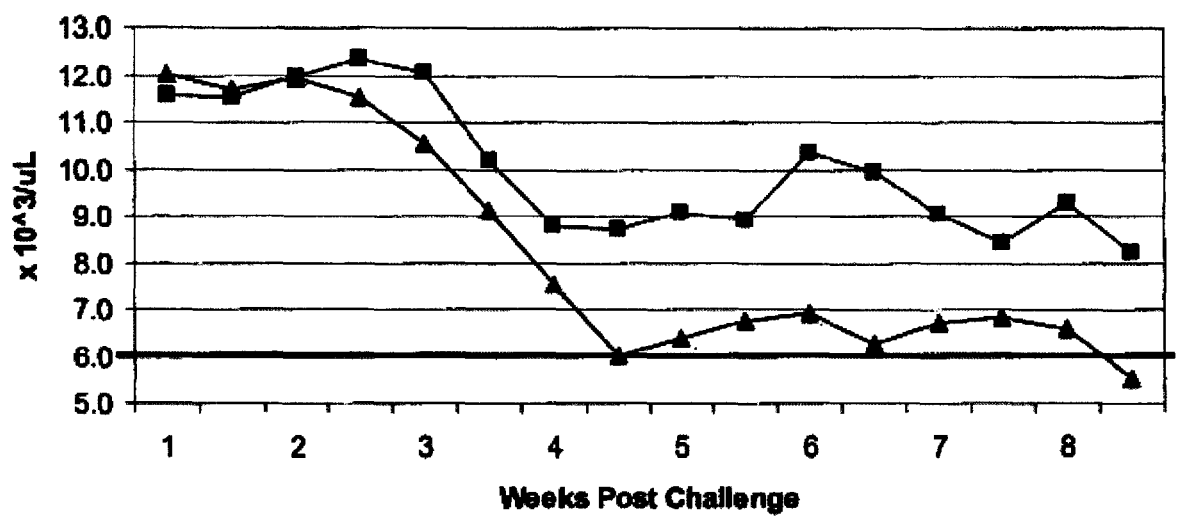
FIG. 1 is a graphical representation of the Mean Post Challenge White Blood Cell Counts over time of control animals (triangles) and vaccinated animals (squares). The bold line indicates the minimum level of white blood cell counts considered normal in accordance with the Merck Manual.

The present invention provides immunogenic compositions and vaccines that can reduce the incidence of thrombocytopenia leucopenia, anemia, and weight loss following a challenge with a virulent strain of *E. canis*. The present results are inconsistent with previous published reports regarding infected dogs, who had been cured by antibiotic treatment, hut were susceptible to subsequent disease [see e.g., Breitschwerdt et al., *Antimicrobial Agents and Chemotherapy* 42(2) 362-368 (1998)]. These prior reports suggest that protective immunity does not develop after exposure to the organism. In direct contrast, the present invention provides methods for the amelioration and/or prevention of canine monocytic ehrlichiosis (CME) and/or tropical canine pancytopenia (TCP), in a subject by administering to the subject an immunogenic composition and/or a vaccine composition of the present invention. Thus, in one aspect the present invention provides an efficacious vaccine against *E. canis*.

As disclosed herein, during the development of an *E. canis* challenge model, dogs rapidly develop a humoral antibody response to *E. canis*. Correlated with the appearance of anti-*E. canis* antibody is a rapid drop in platelet count, or thrombocytopenia, and the initiation of several other clinical indications. However, vaccines that induce strong humoral antibody responses in dogs fail to protect them from clinical signs of disease. Indeed, vaccinated dogs that produce a strong antibody response to *E. canis* may have worse clinical outcomes than non-vaccinated counterparts following challenge. Without being bound to any particular theory, the results disclosed herein appear consistent with *E. canis* using the antibodies produced against it to gain access to the interior of cells through the process of opsonization.

The present invention further provides processes for producing an antigen for an immunogenic composition and/or vaccine itself. In particular embodiments the process comprises growing *E. canis* on a particular cell line to produce the antigen. In some embodiments the antigen is admixed with a veterinarily suitable excipient. In more particular embodiments the present invention includes a composition that comprises an inactivated *E. canis* grown on a dog bone marrow cell line. The immunogenic compositions and/or vaccines of the present invention can further include an adjuvant.

Although the selective mechanism for which *E. canis* discriminates which cells to infect is poorly understood, cells suitable for infection commonly express the Major Histocompatibility Complex (MHC) Class II antigen receptors. Harris et al. [*Vet. Immunol. Immunopathol.,* 96:239-243 (2003)] has demonstrated that *E. canis* possess a mechanism for down-regulating the expression of MHC Class II receptors on the surface of cells that it infects as a possible mechanism for avoidance of immune surveillance. While it is clear that cell lines derived from tick species do not express mammalian MHC Class II receptors, Singu et al. [*Cellular Microbiology,* 8(9), 1475-1487 (2006)] have demonstrated that *E. canis* alters its surface protein expression depending upon whether it is infecting a vertebrate or invertebrate host. Accordingly, in another aspect, the present invention provides cells and/or cell lines that accommodate the growth of *E. canis*, while at the same time yielding an *E. canis* antigen that has been optimized for vaccine use.

As used herein, "subject" refers to any species that can be infected by *E. canis*. In certain embodiments the subject is a non-human animal subject. In particular embodiments the subject is either a canine or a feline. In certain embodiments the animal subject is a canine. In other embodiments the animal subject is a feline.

As used herein the term, "canine" includes all domestic dogs, Canis lupus familiaris or Canis familiaris, unless otherwise indicated.

An "effective immunizing amount," as used herein, may vary depending upon the strain or strains of *E. canis* used to generate the vaccine and may be any amount sufficient to evoke a protective immune response.

Although as used herein, a "protective immune response" can be an immune response in a subject that leads to protection against one or more indications of infection, a "protective immune response" does not require complete protection from any indication of infection. Rather, a "protective immune response" can be an immune response that is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection. The vaccines of the present invention are intended to provide a protective immune response.

As used herein, "eliciting a minimal humoral response" means that administering the vaccine composition comprising *E. canis* in a primary vaccination to a subject (e.g., a canine) does not result in the detection of antibodies to *E. canis* in test sera obtained from the subject 21 days after a primary exposure to the vaccine composition, when that detection is performed by the following procedure: exposing a 1:40 dilution of the test sera to fixed *E. canis*, washing sufficiently to remove all unbound material, adding a fluorescently labeled anti-IgG antibody appropriate to the species of the subject, washing sufficiently to remove all unbound material, and then visually inspecting for fluorescence due to the fluorescently labeled anti-IgG antibodies bound to the fixed *E. canis* via antibodies specific for *E. canis*. In particular embodiments administering to the subject a single subsequent booster vaccination of the vaccine still does not elicit a significant humoral response against *E. canis* and requires a dilution of 1:160 or less of the test sera obtained from the animal subject after the exposure to the booster vaccine composition to detect antibodies to *E. canis* in the test sera, if they are detectable at all, when determined by the method performed for the primary vaccine above.

As used herein, the term "stably-infected" cell line refers to a cell line that remains infected throughout at least 10 passages of cell culture.

Antigens

The *E. canis* antigens of the present invention can be isolated from any number of sources or strains of *E. canis*. Examples of such strains of *E. canis* include, but are not limited to, Ebony, Broadfoot, Florida, Israel 611, Kogashima 1, Louisiana, Oklahoma, Venzuela, North Carolina State University (NCSU) strain Jake, and NCSU isolates Demon, D J, and Fuzzy. In certain embodiments, the antigen may be an *E. canis* bacterin. In additional embodiments, the antigen may be isolated or derived from *E. canis* bacteria that have been inactivated by any suitable method available. Examples of such methods include, but are not limited to, heat, formaldehyde, formalin, bi-ethylene amine, radiation, and beta-propiolactone treatment. In particular embodiments, the *E. canis* bacteria may be inactivated by formalin treatment.

In particular embodiments, the *E. canis* antigen may comprise one or more antigens that will not be recognized as foreign by a subject when the one or more antigens are provided to a subject, i.e., the subject will either not mount a humoral response or will mount a minimal humoral response to the one or more antigens. In some embodiments the one or more *E. canis* antigens will not elicit production of antibodies, or alternatively, will elicit minimal production of antibodies against the one or more *E. canis* antigens. In addition, such *E. canis* antigens will elicit a protective immune response against the one or more *E. canis* antigens. The present invention includes an immunogenic composition for vaccinating a canine against ehrlichiosis of the type comprising an agent that leads to an immune response in the canine, utilizing, as an agent, one that elicits little to no humoral immune response in the canine, yet still elicits a protective immune response in the canine. In particular embodiments this protective immune response is due at least in part to a cell-mediated immune response.

Cells

*E. canis* bacteria of the present invention can be grown on an appropriate cell and/or on cell line. Accordingly, an antigen from *E. canis* may be produced from *E. canis* bacteria grown on or propagated on a cell line. Examples of such cells and cell lines include primary cells (e.g., macrophage) and/or cell lines/continuous cell lines such as those listed below:

Primary Cell Lines:
  Canine blood macrophages, see e.g., [Nyindo, et, al, *Am. J. Vet. Res.* 32:1651-1658 (1971)].
  Peritoneal macrophages, see e.g., [Stephenson and Osterman, *Am. J. Vet. Res.* 38:1815-1819 (1977)].
Continuous Cell Lines:
  Human/dog hybrid cell line, [see e.g., Stephenson and Osterman, *Am. J. Vet. Res.* 41:234-240 (1980)].
  Canine macrophage cell line (DH-82), [see e.g., Dawson, et. al., *J. Infect. Dis.* 163:564-567 (1991)].
  Mouse peritoneal macrophage; Mouse/dog hybrid cell line (MDH-SP), [see e.g., Holland and Ristic, Abstr 55, p. 89, in Program and Abstracts of the IVth International Symposium on Rickettsiae and Rickettsial Diseases, Piestany Spa, Czech and Slovak Federal Republics (1990)].
  Mouse macrophage cell line, [see e.g., Keysary, et. Al., *J VEt Diagn Invest* 13:521-523 (2001)].
  Dog bone marrow cell line (DBM cells), [see e.g., Gaunt et. al. *J. Clin Micro.* 34 (6):1429-1432 (1996)].
  Feline embryonic fibroblast cell line (FEF), [see e.g., Battles et. al., WO 2009/036177 A1].
  Tick cell lines (IDES and ISE6), [see e.g., Munderloh, et. al. U.S. Pat. No. 5,869,335].

In one aspect of the invention the cell line is a macrophage-like cell line, which expresses surface receptors similar to those expressed by canine macrophages. In related embodiments the cell line is a macrophage cell line. In particular embodiments of this type, the cell line employed is the DH-82 cell line, which has the ATCC accession No. CRL-10389.

The present invention includes *E. canis* that had been grown on a monocytic or macrophage-like mammalian cell line. In certain instances these cell lines have been immortalized so as to provide a continuous and reliable growth substrate for the manufacture of vaccines. Immortalized cells may be created from neoplastic progenitor cells such as the DH-82 cell line described by Wellman et al, [*In Vitro Cell Develop Biol* 24:223-228, (1988)]. Cells may be immortalized by the use of viral genes. The simian virus 40 (SV40) T antigen has been shown to be a very reliable way to create immortalized cells and somatic cell hybrids of canine peritoneal macrophages hybridized with SV40 transformed human cells were used to grow *E. canis* in a continuous manner by Stephenson et al. [*Am J Vet Res* 41(2):234-40, (1980)]. A wide range of agents can be used to immortalize cells including different viruses, x-rays, organic solvents, metal compounds and nucleic acids. These methods have been extensively reviewed by Rhim [*Annals NY Acad of Sci.* 919:16-25 (2000)]. In certain embodiments of the present invention *E. canis* is grown in such cell lines and then inactivated to form an *E. canis* bacterin antigen.

In certain embodiments, the cell line is a Dog Bone Marrow (DBM) cell line. In particular embodiments, the DDM cell line is the one described by Gaunt et al. [*J. Clin. Microbio.* 34 (6): 1429-1432, (1996)]. In particular embodiments the DBM cell line is the deposited strain ATCC accession No. PTA-10545. In certain embodiments that cell line is a DBM cell line that is stably infected with *E. canis*. In a particular embodiment of this type the cell-associated *E. canis* is deposited and has the ATCC accession No. PTA-10546. In alternative embodiments, the cell line is an insect cell line. In particular embodiments of this type, the insect cell line is a tick cell line. In one particular embodiment, that insect cell line is the IDE8 tick cell line, isolated from *Ixodes scapularis*, which is deposited with the ATCC and has the ATCC accession No. CRL-11973.

Propagation of *E. canis*

A cell culture infected with *E. canis* may be grown in flasks, and subsequently passed to larger flasks to obtain larger volumes of material required to make immunogenic compositions and/or vaccines. Alternatively, the infected cell culture may be passed from flasks into subsequent roller bottles, spinner flasks, cell cubes, bioreactors, or any apparatus capable of growing cell culture on large scale in order to produce a suitable quantity of material required to blend an immunogenic composition and/or a vaccine. Infected cultures may be frozen down in a suitable media and used for infection of cell culture later.

Cells can be adherent and attached to the growth flask or apparatus, including attached to microcarriers, or alternatively, floating in suspension. Methods for removing adherent cells include, but are not limited to, scraping manually from the flask using mechanical cell scrapers or treating with a trypsin solution to remove them from the flask and subsequently neutralizing the unused trypsin with a protein solution. Cells may then be centrifuged to concentrate and resuspended in a suitable freezing media. Freezing medias include, but are not limited to, medias containing 10-90% fetal calf serum and 1-20% dimethyl sulfoxide (DMSO). Other suitable cryopreservatives may be used which may be more suitable for the different cell lines and result in a high level of viability upon thawing and re-starting the culture.

In order to start an infected culture, non-infected cells may be removed from the freezer and cultured in a suitable media. For example, a 1 mL vial containing $1\times10^5$ DBM cells is rapidly thawed and placed into a T-75 tissue culture flask (75 $cm^2$ surface area) containing a suitable media for growth of DBM cells. In one particular embodiment, the media is Fischer's complete growth media. One liter of Fischer's complete growth media for DBM cells, for example, is made by adding 200 ml/mL of horse serum to 770 ml/mL of Fischer's media. The media is completed by adding 10 mLs of a 2 mg/mL hydrocortisone solution, 10 mLs of a 200 mM glutamine solution, and 10 mLs of a 1M 1-1M HEPES solution.

Once the DBM culture reaches a suitable level of confluence (10-90%), the culture is ready to be infected. A vial of infected culture is removed from the freezer, rapidly thawed and dispensed onto the growing culture. The culture is grown at 36±2° C. in capped or vented flasks with or without $CO_2$ supplementation. The culture is maintained according to common methods for one skilled in the art by passing the cells into fresh media as required. After several weeks, the culture may be checked for the level of infection by indirect fluorescence microscopy using anti-*E. canis* antibodies or other suitable methods. Cultures may reach a level of infection of 90% or higher. A higher level of infection is more desirable as it results in a higher yield of antigenic material per volume of culture. The infected culture may be passed to larger volumes of culture by movement of the culture to larger flasks, roller bottles, or other suitable culture vessels.

Infection of the cell culture by *E. canis* can be determined by several methods including, but not limited to, microscopic analysis of cells stained with dyes such as Giemsa stain, Cameo Difquick stain or acridine orange. In addition, antibodies specific for *E. canis* can either be directly or indirectly labeled with fluorescent markers and viewed with a fluorescent light microscope and at a suitable wavelength for the particular fluorescent marker. Other techniques can be used to determine the level of infection of the culture including, but not limited to, quantitative polymerase chain reaction (qPCR) or PCR.

Uninfected cells may be added to the culture as needed in order to maintain a certain level of infection in the culture. When a suitable volume of infected culture is reached, the culture may be inactivated by a variety of methods including, but not limited to, heat or chemical methods. Prior to inactivation, the culture may be titrated to determine the amount of infectious particles in the culture as a method of determining how much post-inactivated culture to add to the blend. A method for titrating an infected culture is provided in the Examples below. In certain embodiments, formalin is added to the culture to a final concentration of 0.05% and the culture is mixed for three days at 36±2° C. Other such inactivants that may be used include, but are not limited to: ethyleneimines (EI, BEI), beta propiolactone and phenol. Antibiotics may also be used to inactivate the culture such as deoxycycline or any other antibiotic that *E. canis* is sensitive to.

The culture can be tested by any number of methods to determine viability. Such methods include, but are not limited to, back titration on cell culture, membrane integrity for withstanding non-permeable dyes, and injection into dogs and monitoring for typical signs of infection.

Once inactivated, the culture can be concentrated by any of a number of methods. For example, concentration of the non-viable *E. canis* can be done by centrifugation, ultrafiltration, or evaporation. In one particular embodiment, the DBM cells that are infected with *E. canis* are inactivated and then centrifuged at 1400×g for 15 minutes to pellet the whole cells. The supernatant is discarded and the pellet is resuspended in Fischer's media without serum. Gentamicin, or a similar preservative, may be added post-inactivation to avoid contamination issues. The culture is resuspended in Fischer's media without serum to one tenth of the original volume in order to concentrate the inactivated culture and make it easier to handle. The amount of antigen available in the inactivated concentrate may be determined by any number of methods including chromatography, spectroscopy, or various types of specific immunoassays. The bulk antigen can be blended with diluents and an adjuvant to make an acceptable vaccine.

Immunogenic Compositions and Vaccines

As indicated above, the immunogenic compositions and/or vaccines comprising an antigen of the present invention (e.g., an *E. canis* bacterin) can, but do not necessarily further include one or more pharmaceutically acceptable adjuvants. Examples of pharmaceutically acceptable adjuvants are well known in the art, see, e.g. REMINGTON'S PHARMACEUTICAL SCIENCES, 18th Ed. (1990, Mack Publishing Co., Easton, Pa.) and GOODMAN AND GILMAN'S, THE PHARMACOLOGICAL BASIS OF THERAPEUTICS (10$^{th}$ ed. 2001). In particular embodiments, the adjuvant may be one that stimulates a cell-mediated immune response, but does not stimulate a humoral immune response.

The immunogenic compositions and/or vaccines of the present invention that further comprise an adjuvant can comprise one or more elements not generally soluble in water. In particular embodiments the adjuvant is a non-polar solute dissolved in a non-polar solvent. Examples of non-polar solvents include, but are not limited to, hexane, benzene, toluene, diethyl ether, chloroform, and ethyl acetate. In one such embodiment, the solvent is a chloroform solvent system. Chloroform may be preferred in some instances as it is non-flammable and more suitable for manufacturing veterinary biologicals. An adjuvant exemplified herein is trehalose 6,6'-dimycolate in a chloroform solvent system.

Non-polar solvents are typically not soluble in water and therefore the use of polar solvent with a relatively low dielectric constant, but with good solubility in water may be used in the solvent system to increase the solubility of the adjuvant mixture in an aqueous solution. Examples of polar solvents include, but are not limited to, methanol, ethanol, isopropanol, dimethyl sulfoxide and dimethylformamide. In certain embodiments, the non-polar adjuvant is Cord Factor [e.g., trehalose 6,6'-dimycolate]. Other non-polar adjuvants may be useful in stimulating cell mediated immunity including, but not limited to, hydrophobic fractions of purified saponins, bacterial lipopeptide (Pam$_3$CSK$_4$) and monophosphoryl lipid A. In particular embodiments the Cord Factor is dissolved in a chloroform solvent system. In particular embodiments the chloroform solvent system comprises about 65-95% chloroform volume/volume.

Accordingly, certain embodiments of chloroform solvent systems include, but are not limited to, solvent systems comprising chloroform and methanol. In a non-limiting example, the chloroform solvent system may comprise about 70% to 95% chloroform and/or about 5% to 30% methanol volume/volume. In certain embodiments of this type, the chloroform solvent system further comprises 0.5-5.0% water volume/volume. In one non-limiting example, the chloroform solvent system may comprise ninety parts chloroform by volume, ten parts methanol by volume, and one part water by volume [i.e., about 90% chloroform:10% methanol:1.0% water volume to volume, respectively]. In particular embodiments, the adjuvant may comprise Cord Factor and/or other adjuvants dissolved in a chloroform solvent system. In one such embodiment, the adjuvant is trehalose 6,6'-dimycolate, which is dissolved in the chloroform solvent system: 90 of Chloroform:10 mL of Methanol:1 mL of water.

In particular embodiments, the vaccine composition may comprise one or more pharmaceutically or veterinarily acceptable carrier or diluents. Non-limiting examples of carriers or diluents that may be used in vaccine composition formulations include water, glucose solutions, dextrose/saline, saline, phosphate buffered saline (PBS), HEPES buffer, Fischer's media, Hank's solution, and Ringer's solution. Such formulations may contain pharmaceutically acceptable auxiliary substances to enhance stability, deliverability or solubility, such as buffering agents, tonicity adjusting agents, wetting agents, detergents, and the like. Additives may also include additional active ingredients such as bactericidal agents or stabilizers. For example, the solution may contain thimerosal, gentamicin, sodium acetate, sodium lactate, sodium chloride, potassium chloride, calcium chloride, sorbitan monolaurate, or triethanolamine oleate. Compositions may be sterilized by conventional, known sterilization techniques.

In certain embodiments, it is contemplated the vaccine composition may further comprise other active components such as, but not limited to, an antipathogenic component directed against, or an antigenic component and/or attenuated and/or killed isolate of: rabies virus, Lyme disease (*Borrelia burgdorferi*), canine distemper virus, canine bordetella, canine parvovirus, canine adenovirus, canine coronavirus, *Babesia canis, Anapkisma phagocylophiluin, Giardia; Leptospira interrogans* such as Serovars *canicola, icterohaemorrhagiae, pomona, grippotyphosa* or *bratislava* or the like, or any combination thereof.

In some embodiments, the vaccine and/or immunogenic composition may be formulated in a dosage unit form to facilitate administration and ensure uniformity of dosage. Herein, a dosage unit as it pertains to the vaccine composition refers to physically discrete units suitable as unitary dosages for a subject, each unit containing a predetermined quantity of *E. canis* antigen calculated to produce the desired immunogenic effect in association with an adjuvant, carrier, and/or vehicle. In certain embodiments, the immunogenic composition and/or vaccine is lyophilized.

In certain embodiments the vaccine and/or immunogenic composition can be administered parenterally, for example, intramuscularly, subcutaneously, intraperitoneally, intradermally or the like, or the immunogenic composition and/or vaccine may be administered orally or intranasally in effective amounts according to a schedule determined by the time of potential exposure to a carrier of *E. canis*. In this way, the treated subject may have time to build immunity prior to the natural exposure. For example, a typical treatment schedule may include subcutaneous injection at least 42 days prior to potential exposure. In embodiments, more than one administration of the vaccine composition may be provided to a subject. By way of none limiting example, a first administration at about 42 days and a second at about 21 days prior to potential exposure of the subject. However, the onset of immunity could occur in a more rapid time course.

Administration of Vaccines

Vaccines of the present invention may be administered as a liquid, emulsion, dried powder, including as a lyophilized power, and/or in a mist through any parenteral route, intravenously, intraperitoneally, intradermally, by scarification, subcutaneously, intramuscularly, or inoculated by a mucosal route, e.g., orally, intranasally, as an aerosol, by eye drop, by in ovo administration, or implanted as a freeze dried powder.

ATCC Deposit

A culture of the following biological material has been deposited with the following international depository by:

Board of Supervisors,

Louisiana State University and Agricultural and Mechanical College and LSU Agricultural Center, 104 Efferson Hall, Baton Rouge, La., 70803

American Type Culture Collection (ATCC) 10801 University Boulevard, Manassas, Va. 20110-2209, U.S.A., under conditions that satisfy the requirements of the Budapest Treaty on the International Recognition of the Deposit of Microorganisms for the Purposes of Patent Procedure.

| Organism | ATCC Accession No. | Date of Deposit |
| --- | --- | --- |
| Dog Bone Marrow Cell | PTA-10545 | Dec. 22, 2009 |
| Cell-associated *E. canis* | PTA-10546 | Dec. 22, 2009 |

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLES

Example 1

TABLE 1

| Vaccine composition | |
| --- | --- |
| Antigen Fraction | Volume/Weight Used |
| Formalin-inactivated *E. canis* antigen at a titer of 6.5 $\log_{10}$ TCID$_{50}$/mL | 315 mL |
| Adjuvant: Trehalose 6,6'-dimycolate 100 mg dissolved in Chloroform Solvent System | 101 mL |
| Chloroform Solvent System | |
| Chloroform | 90 mL |
| Methanol | 10 mL |
| Water | 1 mL |
| Fischer's Media | 9479 mL |
| 1M HEPES buffer | 94.9 mL |
| Thimerosal 10% solution | 9.1 mL |
| Gentamicin solution | 0.96 mL |
| Total Blend Volume | 10 L |

Example 2

Study Design and Results

TABLE 2

| Test Animal Description | |
| --- | --- |
| Species | Canine |
| Initial Age | 9-11 months |
| Sex | Female |
| Breed | Laboratory Beagles |
| Initial Body Weight Range | 9.0-16.6 kgs on day of challenge |
| Number of Animals | 16 |
| Identification Method | Ear tattoo |
| Inclusion Criteria | Physical examination by veterinarian prior to study and determined healthy and suitable for use. Serologically negative for antibodies to *E. canis* (≤1:40) prior to first vaccination, normal platelet count values (≥200,000/μL) prior to challenge. |
| Exclusion Criteria | Any animal that did not conform with inclusion criteria. |

Housing and Animal Husbandry

Acclimation/Conditioning: The animals were taken from a preexisting pool and thus no treatments or conditioning were necessary. Animals were acclimated for at least 7 days prior to the start of the study. All animals were subject to normal good husbandry practices through the study and routine procedure were standardized across all animals.

Housing: Dogs were group housed randomly in pens (4-5 dogs per pen) without regard to treatment groups.

Diet: Water was provided ad libitum to all animals. Feed met the minimum nutritional requirements for animals of this age and complied with standard procedures.

TABLE 3

Treatment Group Assignments

| Treatment Group | No. of Dogs | Vaccine | Dose and Route | Vaccination on Study Days | Challenge on Study Day |
|---|---|---|---|---|---|
| 1 | 8 | None | None | None | 42 |
| 2 | 8 | Yes | 1 mL Subcutaneous | 0 and 21 | 42 |

Randomization: The dogs were ranked by generation of a random number within block and then sorted with the group ID linked. The lowest random numbers within blocks were assigned to group 1 and the highest random numbers were assigned to group 2. As weight loss is one of the clinical signs associated with E. canis infection, dogs were also blocked by weight during the randomization.

Blinding of Study: Personnel testing laboratory samples, performing daily animal observations, clinical assessments and performing necropsy observations were unaware of treatment group assignments until study completion.

Experimental Procedures:

Pre-Vaccination Monitoring/Acclimation:

Samples: Blood samples were collected in serum separation tubes on study day 0 prior to first vaccination for antibody titer analysis.

Physical Examination: All animals received a physical examination on day −3 at the test facility by the attending veterinarian and were found to be healthy and suitable for the study.

Daily Observations: During the acclimation period, all animals were observed each day by the animal care staff.

Clinical Observations: Clinical signs and rectal temperatures were recorded on day 0 and 21 prior to vaccination.

Vaccination:

Administration of the Biological Product: The vaccine was administered subcutaneously, in a 1.0 mL dose, to each animal on days 0 and 21 using a 3 mL syringe and 23 gauge×1 inch needle. All vaccines were held on wet ice during transportation to the animal facility and during vaccine administration. Subcutaneous vaccination was performed in the right suprascapular region for the first dose and the left suprascapular region for the second dose.

Post Vaccination Procedures:

Injection Site Reactions: Injection site observations were recorded for 7 days following each vaccination.

Daily Observations: All animals were observed daily during the post vaccination period by the animal care staff.

Serology: On study day 21 blood samples were collected in serum separation tubes for antibody titer analysis.

Pre-Challenge Procedures:

Clinical Observations: Clinical signs and rectal temperatures were taken on study days 35, 39 and 42 (before challenge) to establish baseline values.

Blood Samples: On study day 42 (prior to challenge) blood samples were collected in serum separation tubes for antibody titer analysis. On study days 35, 39, and 42 (prior to challenge) blood samples were collected in EDTA tubes for baseline CBCs. On study day 42 (prior to challenge) blood was collected in PAX Gene tubes for PCR analysis.

Bodyweights were recorded on study day 4 prior to challenge) for baseline values.

Challenge:

Challenge Material: Two vials of E. canis challenge material (low passage frozen culture passaged in dogs) were removed from liquid nitrogen, thawed quickly and diluted 1:100 (1 mL+99 mL) in Fischer's media. The diluted challenge material was stoppered, inverted to mix, and then 1 mL was removed for titration. The vial was sealed with an aluminum cap, labeled and placed on ice in a spill proof secondary container for transport to the animal unit.

Challenge Administration: On day 42 all dogs were challenged subcutaneously with 2.0 mL of diluted challenge material.

Challenge Confirmation/Backtitration: A sample from the diluted challenge material was collected and used for immediate titration on the day of challenge in 24-well tissue culture plates.

Post-Challenge Monitoring:

Body Weights: Body weights were recorded weekly following challenge.

Daily Observations: Animal observations were recorded daily following challenge, except on days when clinical observations and temperatures were performed, until study day 49.

Clinical Observations: From study day 49 until the end of the study, clinical signs (depression, dehydration, epistaxis, and nasal/ocular discharge) were recorded daily and rectal temperatures were recorded twice a week.

Injection Site Reactions: Injection site observations were made for 7 days following challenge.

Blood Samples:

Blood for CBCs: Blood samples (EDTA) were collected two times per week after challenge for monitoring CBC profiles.

Blood for PGR Testing: Blood was collected weekly in PAX Gene tubes for PCR analysis.

Blood for Serum: Dogs were bled once every two weeks following challenge for serology.

Necropsy/Disposition: All test animals were humanely euthanized by intravenous injection of Beuthanasia prior to necropsy.

Sample Collection and Handling:

EDTA Blood for CBCs: Blood was collected by venipuncture of the jugular vein using evacuated tubes containing tripotassium-EDTA. Blood was packaged on ice packs and processed the same day for blood profile analysis.

SST Blood for antibody analysis: Blood was collected by venipuncture of the jugular vein using evacuated tubes. Blood was centrifuged at 2500 RPM for 10 minutes and the serum was labeled and stored at −10° C. or colder.

Blood for PCR Testing: Blood was collected by venipuneture of the jugular vein using evacuated PAX Gene tubes and PCR analysis performed.

Analytical Methods:

Platelet Counts: Platelet counts were determined as per the procedures well established in the art.

E. canis Titration: A retention sample of diluted challenge material was tested. Briefly, DBM cells were prepared in 24 well plates at a concentration of $1.0 \times 10^5$ cells per mL and incubated at 36±2 degrees Celsius for 1 day prior to conducting the assay. The media was aseptically removed from the 1 day old DBM cultures and ten-fold serial dilutions of the challenge material were added, 1 mL per well, into 4 replicate wells of the 24 well plate. Plates were incubated at 36±2 degrees Celsius for 7 days. After 7 days, plates were re-fed with fresh Fischer's growth medium, 1 ml, per well and returned to 36±2 degrees Celsius for 7 days. Upon 14 days of incubation, the plates were centrifuged for 10 minutes at 2000

RPM, the media was aspirated and the cultures were fixed with 100% methanol (0.5 mL per well) for 10 minutes. Once the plates were dry, 0.5 mL per well of mouse anti-*E. canis* monoclonal antibody (diluted 1:1000 in 0.01M PBS) was added and incubated for 30 minutes at 36±2 degrees Celsius. Plates were washed 3 times in 0.01M PBS with a final wash in water. Then 0.5 mL per well of a FITC labeled goat anti-mouse IgG (diluted 1:100 in 0.01M PBS) was added and incubated for 30 minutes at 36° C.±2° C. Plates were washed again and observed under a fluorescent microscope. Titers were calculated at 50% endpoints using the Spearman-Karber method.

Serology: An indirect immunofluorescent antibody (IFA) assay was used for detection of anti-*E. canis* antibody in dog sera. Briefly, initial 1:20 dilutions of serum were prepared in serum dilution buffer. Single samples were diluted to 1:40, 1:80, 1:160 and 1:320 and then added (104, per dilution) to 12 well slides containing fixed *E. canis* infected DBM cells and incubated in a humidified chamber for 30 minutes at 36±2 degrees Celsius. Slides were washed in 0.01M PBS for 10 minutes and 10 μL of FITC labeled goat anti-dog IgG (diluted 1:100 in 0.01M PBS) was added to each well on the slide. Slides were then placed into a humidified chamber for 30 minutes at 36±2 degrees Celsius, washed in 0.01M PBS for 10 minutes and read by fluorescent microscopy. The titer is determined by the highest dilution where fluorescence is visible.

PCR: PCR was performed on the blood samples as per the procedures well established in the art.

Inactivation Testing: Formalin-inactivated antigen was tested to check for complete inactivation. Briefly, DBM cells were prepared in 150 cm$^2$ flasks one day prior to inoculation at $1.0 \times 10^5$ cells per mL and 60 mL per flask. 1.0 mL, of each test sample (including positive and negative controls) was inoculated into the flasks and incubated for 8 days at 36±2 degrees Celsius. Two blind passages were performed, with each passage receiving 10 mL of the previous passage inoculum. At 8 days post-blind pass 2, each flask material was stained by specific immunofluorescence. Lack of fluorescence in cultures is an indication of complete inactivation.

Data Analysis:

Outcome Variables: The primary variable for determination of efficacy of the vaccine formulation was based on prevention of severe thrombocytopenia in vaccinates compared to controls. Percent weight loss, total necropsy score, blood values and clinical signs were considered supporting evidence of protection.

Scoring of Clinical Observations: Clinical signs for each dog were recorded and scored daily for the 12 week period post challenge.

Clinical Assessment Guide: Upon entering the isolation room, walk through to assess the attitude of the animals. The score for depression may be determined in many animals during this first walk. Next proceed with the clinical observations. Then, measure the body temperature followed by obtaining the required blood samples.

Death: 100 points (No vital signs, including dogs that are moribund and euthanized).

Depression: Absent (Normal activity and behavior). Present: Lethargic, lying down while you are in the room, and reluctant to get up.

Nasal Discharge: Normal (Absent); Serious (Moderate to severe): Clear fluid, often watery, all the way down to or below the mouth—either along the sides of the nose or down the nasal philtrum; Mucopurulent (Moderate to severe): Mucopurulent, not clear, often colored discharge all the way down to or below the mouth—either along the sides of the nose or down the nasal philtrum.

Ocular Discharge: Normal (Absent); Serious (Moderate to severe): Clear fluid, often watery, one-halfway down the nose or rimming eye plus pooled up or soaking hair at inner or outer corner of the eye; Mucopurulent (Moderate to severe): Mucopurulent, not clear, often colored discharge one-half way down the nose or rimming eye plus pooled up or soaking hair at inner or outer corner of the eye.

Epistaxis: (Bleeding from nostrils)—Normal(Absent); Present: Bleeding from nostrils.

Dehydration: Normal (Absent); Present: Folds of skin between shoulders stick together or take longer than 3 seconds to retract.

TABLE 4

Scoring System for Specific Clinical Signs

| | |
|---|---|
| Death | 100 |
| Depressed State | 2 |
| Nasal Discharge | |
| Serious Discharge | 1 |
| Mucopurulent Discharge | 2 |
| Ocular Discharge | |
| Serious Discharge | 1 |
| Mucopurulent Discharge | 2 |
| Epistaxis | 2 |
| Dehydration | 1 |

Calculation of Percent Weight Loss: Each dog was weighed prior to challenge to determine a baseline weight. Weight loss for each dog was calculated weekly post challenge using the following formula: ((baseline wt−current wt) baseline wt)×100=% wt loss.

Results and Discussion

Concurrent Disease: One control dog had to be treated during the study. The dog developed an ulcer in its left eye and the eyelid was swollen shut. Antibiotics were avoided so as to not affect the study. The condition was discovered on a particular day. At that time, the eye was flushed with isotonic saline. Two days later the dog received a subcutaneous injection of atropine, locally. Five days after the condition was discovered the dog was observed by the veterinarian to be fully recovered. The condition was likely caused by trauma (scratch from another dog) and not as a result of the study test product or the challenge.

Pre-Vaccination Testing: Dogs were screened for the presence of antibodies to *E. canis* prior to vaccination. All dogs were found to have a titer of <40 when tested by *E. canis* specific immunofluorescent antibody (IFA) assay (See Table 5; Day 42 is the day of challenge). Clinical observations and rectal temperatures were also taken prior to vaccination. All dogs were found to be clinically normal.

TABLE 5

Mean Serology Summary

| Treatment Group | Day 0 | Day 21 | Day 42 | Day 56 | Day 70 | Day 84 |
|---|---|---|---|---|---|---|
| Controls | <40 | <40 | <40 | <40 | ≥147 | ≥320 |
| Vaccinates | <40 | <40 | ≥123 | ≥104 | ≥207 | ≥207 |

Post-Vaccination Testing

None of the vaccinated dogs were observed to have injection site reactions post vaccination. All dogs were observed daily for adverse effects associated with the vaccine after both vaccinations. None of the dogs showed any adverse clinical signs post vaccination.

Blood samples were taken for serology at Day 21 post-vaccination, immediately prior to the second vaccination. Titers were measured using doubling dilutions of serum on 12-well slides coated with *E. canis* infected DBM cells. Dilutions started at 1:40. None of the dogs in the vaccinate group showed a titer over the 1:40 background after a single dose of vaccine (see Table 5).

At Day 42, immediately prior to challenge, the breakdown of the vaccinate *E. canis* antibody titers was as follows (see also, Table 5):

| Titers <40: | 0 dogs |
|---|---|
| Titers =80: | 4 dogs |
| Titers =160: | 3 dogs |
| Titers >320: | 1 dog |

All unvaccinated control dogs remained seronegative (<1:40) prior to challenge.

Challenge: All dogs were challenged on day 42 of the study by diluting the thawed challenge material 1:100 in Fischer's media and administering 2 mL of challenge subcutaneously to each dog. The challenge material was titrated at the time of administration to the dogs and found to have a titer of $10^{3.2}$ $TCID_{50}$ per 2 mL dose.

Post Challenge Clinical Assessment:

Weight Loss Associated with Challenge: Body weights were recorded weekly following challenge. The results are summarized in Table 6.

TABLE 6

| | Mean Body Weights (Kg) Post Challenge | | | | | | | | |
|---|---|---|---|---|---|---|---|---|---|
| Treatment Group | Baseline Day 42 | Wk 1 Day 49 | Wk 2 Day 56 | Wk 3 Day 63 | Wk 4 Day 70 | Wk 5 Day 77 | Wk 6 Day 84 | Wk 7 Day 91 | Wk 8 Day 98 |
| Controls | 13.3 | 13.4 | 13.4 | 13.2 | 12.8 | 11.9 | 11.4 | 11.5 | 11.5 |
| Mean Percent Weight Loss | | | | | 3.89% | 11.15% | 14.83% | 16.97% | 15.91% |
| Vaccinates | 10.8 | 10.8 | 10.9 | 10.6 | 10.2 | 9.9 | 9.8 | 9.9 | 9.9 |
| Mean Percent Weight Loss | | | | | 4.86% | 7.29% | 7.88% | 7.85% | 7.61% |

The highest percent weight loss was seen in the control dogs with a mean of 16.97% reduction in body weight at 7 weeks post challenge. This was also the point where there was the greatest difference between the treatment groups as the vaccinates only experienced a 7.85% drop in body weight. Weight loss was examined statistically. Severe weight loss was defined as ≥15% of the dog's body weight. Eighty-seven percent (7/8) of the control dogs had weight lost ≥15% of their body weight, compared to 12% (1/8) of the vaccinates. This difference is extremely significant (p=0.0042).

Mortality: Two of eight (25%) dogs in the control group were euthanized due to severity of clinical signs. None of the vaccinates died during the trial. Euthanasia was a judgment call of the veterinarian based upon clinical signs, weight loss and blood cell and electrolyte values. The attending veterinarian was blinded to the group designation. The difference was supportive, but not significant due to the low number of dogs in the study (p=0.2118).

Complete Blood Count Evaluation: Blood samples were also taken on study days 35, 39, and 42 to set baseline values for white and red blood cells (WBC and RBC), hematocrit (HCT), hemoglobin (1-10) and platelets. All dogs were in the normal ranges for these measurements prior to challenge according to the Merck Veterinary Manual, Eighth Edition [Merck and Co. Inc., Whitehouse Station, N.J., USA, (1998)].

Blood samples collected twice a week post challenge. CBC results included White Blood Cells (WBC's), Red Blood Cells, (RBC's), Hemoglobin (Hub), Hematocrit (Hct or Packed cell volume) and platelets. Because *E. canis* has such a dramatic effect on blood values, a scoring system was developed that would rate the incidence as "normal, abnormal, or clinically significant (or severe). Table 7 summarizes the values used in this study.

TABLE 7

| Summary of Results of Blood Samples | | | | |
|---|---|---|---|---|
| | Units | Dog Values (normal) | Abnormal Values | Clinically Significant "Severe" Values* |
| WBC | ×10³/μL | 6-17 | <6.0 | ≤4.5 for multiple days |
| RBC | ×10⁶/μL | 5.5-8.5 | <5.5 | ≤4.0 for multiple days |
| Hgb | g/dL | 12-18 | <12 | ≤8 for multiple days |
| Hct | % | 37-55 | <37 | ≤28 for multiple days |
| Platelets | ×10³/μL | 200-900 | <200 | <150 for multiple days |

*Merck Veterinary Manual

Clinically significant (or severe) values are calculated as roughly 75% of the low end of the normal ranges for multiple days. Dogs in this range were often observed as having clinical signs which may be directly correlated to the deficiency of the related blood cells. Abnormal values are any value under the minimal level for normal.

Figure 5:
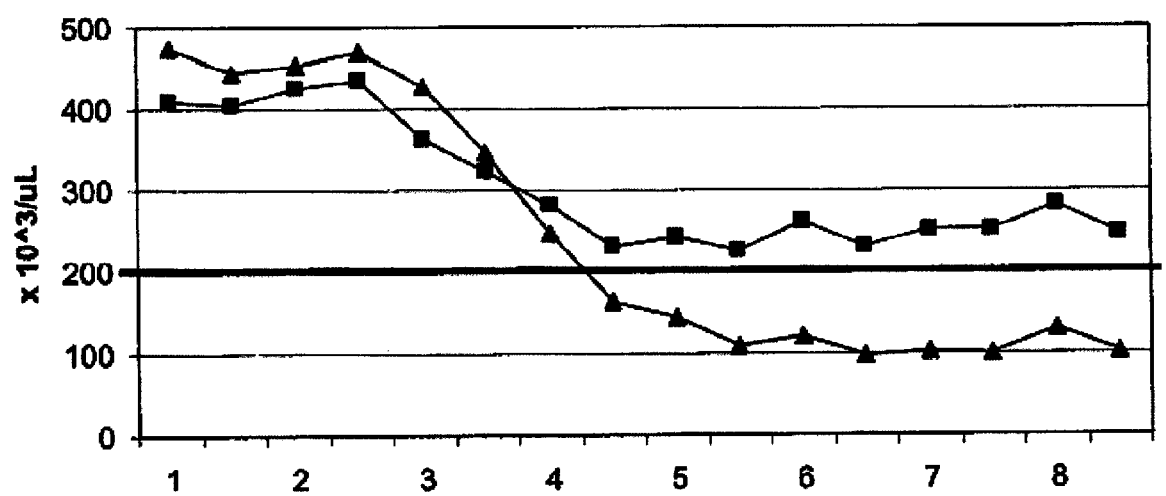
FIG. 5 is a graphical representation of the Mean Post Challenge Platelet Counts over time of control animals (triangles) and vaccinated animals (squares). The bold line indicates the minimum level of platelet counts considered normal in accordance with the Merck Manual.

Platelets: Low platelet counts are the primary clinical sign associated with rickettsial infections. For this study, it was the primary variable. *E. canis* is particularly good at causing very severe drops in platelet numbers in effected dogs. All 8 (100%) control dogs and 5/8 (63%) vaccinates developed thrombocytopenia (platelet counts <200,000/μL). FIG. 5 shows the mean platelet counts (controls vs. vaccinates) post challenge and Table 8 provides a summary of the data. Dogs that had platelet counts of less than 150,000 platelets/μL of blood for two or more readings were considered in the severe category and are at a high risk for bleeding upon injury. The animal care workers could easily identify these dogs as the injury associated with venipuncture bleeds persists for a considerable amount of time after the sample is taken. For the control dogs, 6 of 8 (75%) had platelet counts in the severe category. Only 2/8 (25%) of the vaccinates had counts in the severe category. Statistically, this difference was not significant (p=0.0768). However, mortality in at least one control dog censored the data because the dog died early in the study as it was displaying severe thrombocytopenia. Had the dog not died, the study would have concluded that at least 7/8 controls displayed severe thrombocytopenia. Because mortality is a much more severe clinical sign than thrombocytopenia, the primary variable was re-analyzed as thrombocytopenia or mortality. Taking mortality into account, the difference between controls and vaccinates becomes significant (p=0.0213)

TABLE 8

Summary of Platelet Results

| | Classification | | |
|---|---|---|---|
| | Mild Percent dogs with Thrombocytopenia as defined by the Protocol (<50% of Baseline Count) | Abnormally Low* Percent Dogs with Platelets <200* | Clinically Significant Percent Dogs with Platelets ≤100 for more than one day |
| Controls | 100% (8/8) | 100% (8/8) | 75% (6/8) |
| Vaccinates | 63% (5/8) | 63% (5/8) | 25% (2/8) |

*As defined by the Merck Manual as Thrombocytopenia

Figure 2:
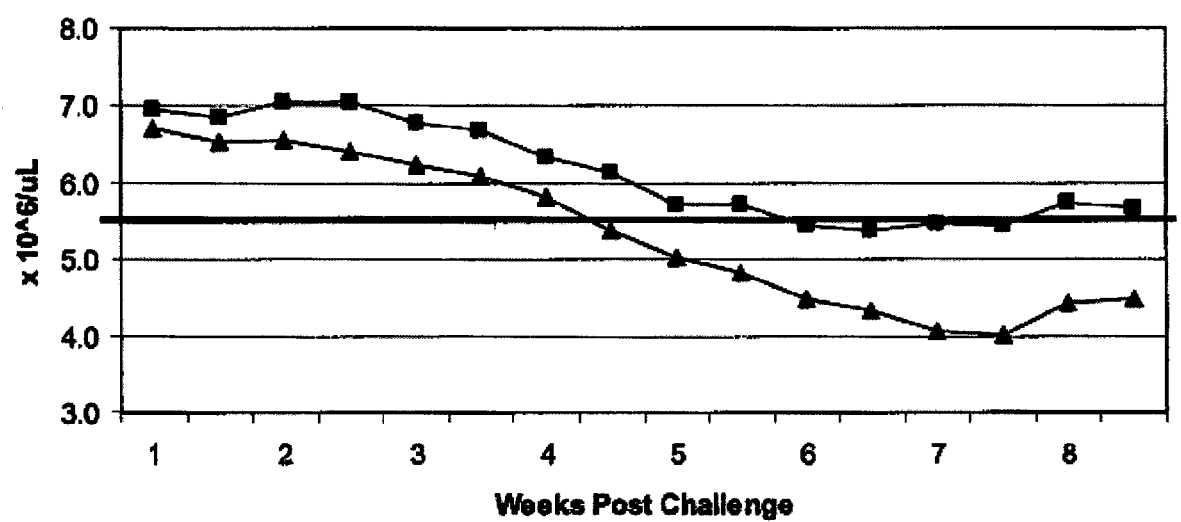
FIG. 2 is a graphical representation of the Mean Post Challenge Red Blood Cell Counts over time of control animals (triangles) and vaccinated animals (squares). The bold line indicates the minimum level of red blood cell counts considered normal in accordance with the Merck Manual.

Red Blood Cells: FIG. 2 shows the mean erythrocyte counts for the period post challenge. FIG. 2 shows that the mean of the control dogs was below normal for most of the trial period, where the mean of the vaccinates stayed in the normal range for most of the trial period. Table 9 illustrates the severity of the challenge as 100% of the control dogs met the Merck Manual's definition of anemic and 63% progressed to the severe category. None of the vaccinated dogs progressed to the sever category of anemia. This difference is very significant (p=0.0081).

TABLE 9

Summary of RBC Results

| | Classification | |
|---|---|---|
| | Abnormally Low* Percent Dogs with RBC count <5.5 × 10$^6$/μL | Clinically Significant Percent Dogs with RBC counts ≤4.0 × 10$^6$/μL for more than one day |
| Controls | 100% (8/8) | 63% (5/8) |
| Vaccinates | 50% (4/8) | 0% |

*As defined by the Merck Manual as anemic

White Blood Cells: FIG. 1 summarizes the results of the leukocyte counts for the period post challenge. FIG. 1 shows a severe decrease in white cell count was observed in the controls. The data is best summarized in Table 10 where a marked difference for both mild and severe leucopenia is observed in the dogs. 38% of the dogs in the control group progressed to the "severe" category of leucopenia where none of the vaccinates did. This difference is not significant (p=0.0822). Table 10 and FIG. 1 illustrate a difference between the means for the vaccinates and controls. The mean of the controls fell below the minimal level for normal where as the mean of the vaccinates did not. This trending suggests that with more animals in each study group, the difference is likely to be significant.

TABLE 10

Summary of WBC Results

| | Classification | |
|---|---|---|
| | Abnormally Low* Percent Dogs with WBC count <6 × 10$^3$/μL | Clinically Significant Percent Dogs with WBC counts ≤4.5 × 10$^3$/μL for more than one day |
| Controls | 88% (7/8) | 38% (3/8) |
| Vaccinates | 50% (4/8) | 0% |

*As defined by the Merck Manual as Leukopenic

Figure 3:
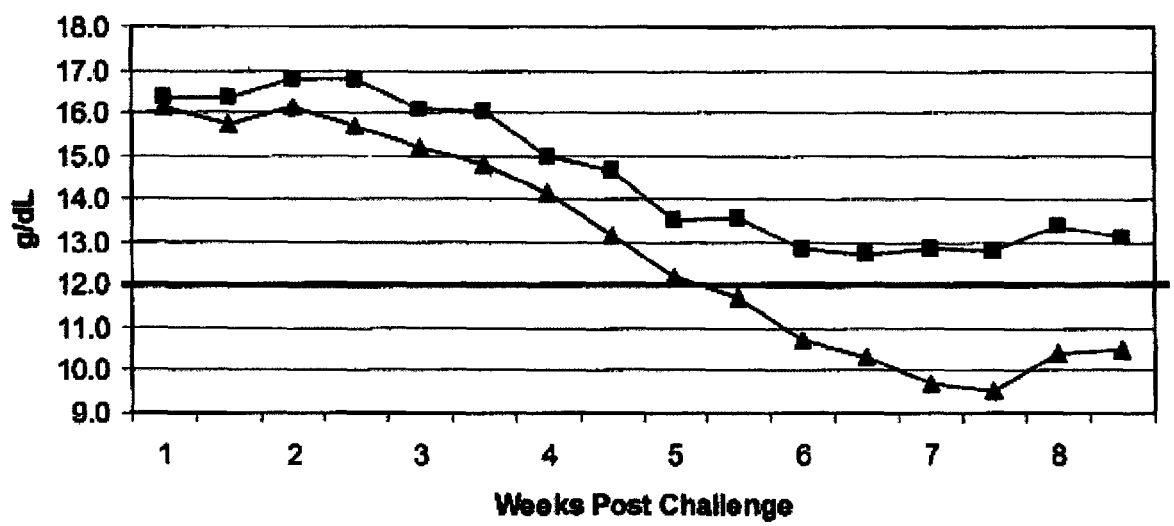
FIG. 3 is a graphical representation of the Mean Post Challenge Hemoglobin Values over time of control animals (triangles) and vaccinated animals (squares). The bold line indicates the minimum level of hemoglobin count considered normal in accordance with the Merck Manual.

Hemoglobin Values: FIG. 3 summarizes the results of the hemoglobin measurements post challenge. Consistent with other blood parameters, FIG. 3 shows that the mean of the controls fell far below minimum values for much of the post challenge period. The vaccinate group mean never went below normal. Table 11 shows that 100% of the control dogs had low hemoglobin values, where only 50% of the vaccinates fell to this level. None of the vaccinates progressed to the severe category for hemoglobin levels. However, only 25% of the controls progressed to the severe category and this difference was not significant (p=0.2118).

TABLE 11

Summary of Hemoglobin Results

| | Classification | |
|---|---|---|
| | Abnormally Low* Percent Dogs with Hgb values <12 g/dL | Clinically Significant Percent Dogs with Hgb values ≤8 g/dL for more than one day |
| Controls | 100% (8/8) | 25% (2/8) |
| Vaccinates | 50% (4/8) | 0% |

*As defined by the Merck Manual as anemic

Figure 4:
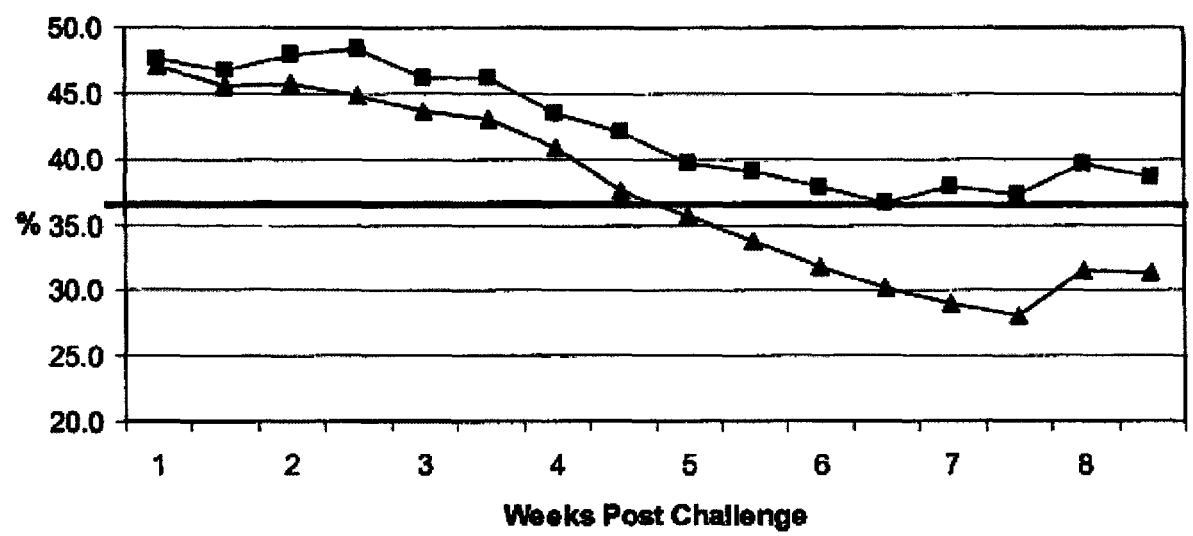
FIG. 4 is a graphical representation of the Mean Post Challenge Hematocrit Values over time of control animals (triangles) and vaccinated animals (squares). The bold line indicates the minimum level of hematocrit count considered normal in accordance with the Merck Manual.

Hematocrit Percentages: FIG. 4 summarizes the results of the hematocrit values post challenge. As with the other measures of anemia, FIG. 4 shows that the control mean ran well below normal for the last half of the challenge period, where the vaccinate dog mean never goes below normal. Table 12 shows that vaccination of dogs with the test product dropped the incidence of anemia, as measured by hematocrit counts, by half. Sixty three percent (⅝) of the control dogs progressed to the severe category for hematocrit where as only ⅛ dogs in the vaccinate group (13%) had a severe value. This difference was very close to significance (p=0.0534).

TABLE 12

Summary of Hematocrit Results

| | Classification | |
|---|---|---|
| | Abnormally Low* Percent Dogs with Hct values <37% | Clinically Significant Percent Dogs with Hct values ≤28% for more than one day |
| Controls | 100% (8/8) | 63% (5/8) |
| Vaccinates | 50% (4/8) | 13% (1/8) |

*As defined by the Merck Manual as anemic

Clinical Signs: Each dog was observed daily for clinical signs indicative of a serious infection. The results are summarized in Table 13. Clinical sign scoring was based upon observations made by blinded personnel observing the dogs for signs of depression, nasal discharge, ocular discharge, epistaxis, dehydration and death. A score was assigned to each observation relative to the severity of the clinical sign.

weekly PCR analysis of the blood for E. canis infection post challenge are in Table 15. All control dogs were positive for E. canis in the blood at more than one time point. PCR never detected E. canis in three of the vaccinates. These results exactly match the results of the platelets as these same dogs failed to develop thrombocytopenia post challenge. The difference between controls and vaccinates for a positive result was not significant (p=0.0822).

TABLE 15

Percentage of Animals Infected with E. canis after Challenge based upon PCR

| Treatment Group | | Day 42 | Week 1 Day 49 | Week 2 Day 56 | Week 3 Day 63 | Week 4 Day 70 | Week 5 Day 77 | Week 6 Day 84 | Week 7 Day 91 | Week 8 Day 98 |
|---|---|---|---|---|---|---|---|---|---|---|
| Controls | % Positive | 0% | 0% | 0% | 50% | 88% | 100% | 100% | 75% | 75% |
| Vaccinates | % Postive | 0% | 0% | 0% | 50% | 63% | 63% | 63% | 50% | 63% |

The total score for the control group was 254 versus 28 for the vaccinates. The mean score for controls versus vaccinates was 32 and 4, respectively. In spite of appearing very indicative of protection, the difference between the groups was not significant (p=0.4364).

TABLE 13

Summary of Clinical Scores

| Group | Total Score | Average | Median |
|---|---|---|---|
| Controls | 254 | 32 | 5 |
| Vaccinates | 28 | 4 | 1 |

Rectal Temperatures: Rectal temperatures were taken and recorded twice a week. Dogs were considered to be febrile if the rectal temperature was >39.5 degrees Celsius. This is consistent with the Merck Veterinary Manual, which lists the normal temperature range as 38.9±0.5 degrees Celsius. E. canis is known for causing temperature spikes in affected dogs. Observations from this study are consistent with this and are summarized in Table 14. 87.5% (7/8) of the controls had fever spikes as compared to 50% (4/8) of the vaccinates. Fever spikes were compared statistically for differences. Twenty five percent (2/8) of the controls had fevers for two or more days whereas only 12.5% (1/8) of the vaccines did. This difference was not significant (p=0.6709).

TABLE 14

Summary of Rectal Temperatures

| Group | Percent of Dogs w/Fever | Percent of Dogs w/Fever multiple days |
|---|---|---|
| Controls | 87.5% (7/8) | 25% (2/8) |
| Vaccinates | 50% (4/8) | 12.5% (1/8) |

*Fever as defined as rectal temp ≥39.5° C.

Challenge Injection Site Reactivity: Dogs were observed for reactivity at the site of challenge. None of the 16 dogs in either the vaccinate group or the control group showed any sign of reactivity at the site of challenge administration.

Results of PCR Detection of E. canis in the Blood: Blood samples were taken for PCR analysis to determine E. canis infection immediately prior to challenge. PCR results are shown in Table 15. As expected, all dogs remained negative for E. canis infection prior to challenge. Results for the Serology Post Challenge: Serology was performed every two weeks post challenge. The serology results for the vaccinated dogs answers the question of whether the dogs in this group that were negative by PCR and failed to develop clinical signs including thrombocytopenia post challenge were actually exposed to E. canis. At some point past day 42 (day of challenge) all three of these dogs have a rapid rise in titer, indicating exposure to the challenge material. A summary of the means for the serology is shown in Table 5. The relevance of antibody titer to protection is not clear from this study. Serology does appear to be a good indicator of exposure to virulent E. canis.

Necropsy Scores: Necropsies were performed on all dogs at the time of euthanasia and persons performing necropsies were blinded. For most of the dogs, this was at eight weeks post challenge. For dogs that had to be euthanized early, due to severe clinical signs, necropsies were performed at the time of death. Dogs were necropsied and scored immediately after euthanasia. Splenomegaly is the one observation that may be clearly associated with E. canis infection. Vaccination status appeared to have an effect on the observations of splenomegaly (Table 16). None of the vaccinated dogs had splenomegaly as compared to 38% (3/8) for the controls. This difference was not significant (0.0822). In dogs that had to be euthanized prior to the end of the 8-week trial, the Attending Veterinarian noticed that there was a consistent finding of accumulation of abdominal fluid. Since low serum albumin levels lead to an osmotic imbalance between the circulation and the tissues, fluid accumulation in the abdominal cavity may result. For the remainder of the trial period, chemical panels were ordered to be performed on the bi-weekly blood samples being sent in for testing. The results of these tests for albumin levels are summarized in Table 17. Half of the controls (4/8) had significant accumulation of fluid in the abdominal cavity observed at necropsy. Of the controls that did have fluid accumulation, 50% of them had a severe rating of more than 200 mL of fluid recovered. None of the vaccinates had any fluid accumulation (Table 16). This difference was not significant (p=0.2118). There was an interesting correlation with the serum albumin levels and platelet counts. All of the dogs that developed thrombocytopenia had below normal albumin values. The vaccination status appeared to clearly effect the serum albumin levels with 6/8 controls (75%) falling below 75% of the minimum value for albumin concentration in the serum where only 3/8 (25%) of vaccinates dropped to this level (Table 17).

TABLE 16

Summary of Necropsy Findings

| External Appearance | Abdominal Fluid | Spleen | Lungs | Stomach | Descending Colon | #Total Necropsy Score |
|---|---|---|---|---|---|---|
| Percent of Control Dogs Affected ||||||||
| 38% | 50% | 38% | 13% | 38% | 0% | 26 |
| Percent of Vaccinated Dogs Affected ||||||||
| 25% | 0% | 0% | 13% | 50% | 38% | 18 |

Total Necropsy Score for the 8 animals in each group

TABLE 17

Summary of Serum Albumin Results

| | Classification ||
|---|---|---|
| | Abnormal Percent Dogs with Serum Albumin <2.5%* | Clinically Significant Percent Dogs with Serum Albumin <1.9 more than one day |
| Controls | 100% (8/8) | 50% (4/8) |
| Vaccinates | 75% (6/8) | 38% (3/8) |

*As defined by the Merck Manual as the lower limit
**"Clinically Significant" is defined as 75% of the minimal value for more than one day Summary Table of all Results: To try and capture the severity of all of these complex results, a summary table was created (Table 18). In this table, only the clinically significant (severe) scores are examined for each parameter measured in this trial. The mean severity score for controls is 14.6 compared to 3.5 for the vaccinates. This dramatic difference highlights the efficacy of the test product in all vaccinates vs. controls.

Conclusions

The challenge was effective and more potent than planned as 100% of the controls developed thrombocytopenia, high titers to *E. canis*, severe clinical signs, weight loss and two of the dogs had to be euthanized.

When taking into account censoring due to mortality, the incidence of severe thrombocytopenia, the primary variable, was shown to be less in the vaccinates than in the controls and that difference was significant (p=0.0213).

Vaccination appeared to have an effect on mortality as 25% of the controls and none of the vaccinates had to be euthanized for humane reasons post challenge.

Severe weight loss was experienced by the dogs in the control group with some dogs losing almost 25% of their body weight during the eight weeks post challenge. The incidence of severe weight loss was less in vaccinates than controls and that difference was extremely significant (p=0.0042).

The difference between vaccinates and controls for other blood parameters that reached severe levels were not quite significant although some were very close. Those included WBCs (p=0.08221), hematocrit (p=0.0534), and hemoglobin (p=0.2118).

PCR detection of *E. canis* in the blood accurately matched the results achieved for the incidence of thrombocytopenia.

Three of the dogs in the vaccinate group never showed any clinical signs of infection or had a detectable level of *E. canis* in the blood by PCR. However, the serology indicated that these three dogs appeared to have an anamnestic response to *E. canis* post challenge, indicating that they were exposed to the virulent challenge material.

Fluid accumulation in the abdomen as a result of severe albumin deficiencies in the blood was only seen in the control dogs and not in the vaccinates.

Clinical signs including depression, nasal discharge, ocular discharge, epistaxis, dehydration and death were the most severe in the control dogs compared to the vaccinates, however, the differences were not significantly different between groups (p=0.4364).

Rectal temperature spikes post challenge were more common in the control dogs.

Neither the vaccination or challenge injections produced any observable reaction on the dogs.

Upon necropsy, the observation of splenomegally was only seen in the controls.

These results support the efficacy of the vaccine of the present invention.

TABLE 18

Summary of all Results in the Severe Category

| Treatment Group | Weight Loss | WBC | RBC | PCV | Hemoglobin | Platelet | Mortality | Fever | Abdominal Fluid | Splenomegally | Albumin | PCR +/- | #Total Score |
|---|---|---|---|---|---|---|---|---|---|---|---|---|---|
| Controls | 21 | 9 | 15 | 15 | 6 | 18 | Yes | 4 | 6 | 3 | 12 | 8 | 117 |
| Vaccinates | 3 | 0 | 0 | 3 | 0 | 6 | No | 2 | 0 | 0 | 9 | 5 | 28 |

Weight Loss - >15% Body Weight = 3
WBC - two or more days ≤4.5 × $10^3$/μL = 3
RBC - two or more days ≤4.0 × $10^6$/μL = 3
Hematocrit/PCV - two or more days ≤28% = 3
Hemoglobin - two or more days ≤8 g/dL = 3
Platelets - two or more days ≤100 × $10^3$/μL = 3
Fever - Temp ≥39.5 two or more days = 2
Abdominal Fluid - >200 mls = 3
Splenomegally - yes = 1
Albumin - two or more days ≤1.9 g/dL = 3
PCR = positive anytime during study = 1
Total Score for the 8 animals in each group It is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

What is claimed is:

1. A vaccine composition comprising an effective immunizing amount of an inactivated *Ehrlichia canis* (*E. canis*); wherein the vaccine comprises a non-polar solvent that comprises a lipophilic adjuvant; wherein the *E. canis* is inactivated with formalin; and
wherein the inactivated *E. canis* elicits a protective immune response, but elicits a minimal humoral response in a subject when the vaccine is administered as a primary vaccine.

2. The vaccine composition of claim 1, wherein the *E. canis* is grown in a canine cell.

3. The vaccine composition of claim 2, wherein the canine cell is a dog bone marrow cell.

4. The vaccine composition of claim 2, wherein the canine cell has the ATCC accession No. PTA-10545.

5. The vaccine composition of claim 1, wherein the lipophilic adjuvant comprises trehalose 6,6'-dimycolate.

6. The vaccine composition of claim 1, wherein the non-polar solvent is a chloroform solvent system.

7. The vaccine composition of claim 6, wherein the chloroform solvent system comprises about 65-95% chloroform volume/volume.

8. The vaccine composition of claim 7, wherein the chloroform solvent system further comprises about 5.0-30% methanol volume/volume.

9. The vaccine of claim 8 wherein the chloroform solvent system comprises about 90% chloroform:10% methanol: 1.0% water volume to volume, respectively.

10. A vaccine composition comprising
(a) a formalin-inactivated cell-associated *Ehrlichia canis* (*E. canis*) that had been grown in a cell having the ATCC accession No. PTA-10545: and
(b) an adjuvant comprising trehalose 6,6'-dimycolate dissolved in 90:10:1 chloroform:methanol:water.

11. A cell comprising an *Ehrlichia canis* (*E. canis*) that has the ATCC accession No. of PTA-10546.

12. A cell that has the ATCC accession No. of PTA-10545.

13. A method of vaccinating a subject against *E. canis*, comprising administering the vaccine composition of claim 1 to the subject.

14. A method of vaccinating a subject against *E. canis*, comprising administering a first dose of the vaccine composition of claim 1 to the subject; and
administering a second dose of the vaccine composition about 21 days after the administration of the first dose of the vaccine composition.

15. A process for producing the vaccine composition of claim 1 comprising
(a) growing *E. canis* in a canine cell;
(b) inactivating the *E. canis* with formalin;
(c) concentrating the inactivated *E. canis*; and
(d) admixing the inactivated *E. canis* with a non-polar solvent that comprises a lipophilic adjuvant.

16. The process of claim 15, wherein the canine cell has the ATCC accession No. of PTA-10545.

17. The process of claim 15, wherein the lipophilic adjuvant comprises trehalose 6,6'-dimycolate.

18. A method of vaccinating a subject against *E. canis*, comprising administering the vaccine composition of claim 10 to the subject.

* * * * *